United States Patent [19]
de Bok

[11] 3,938,369
[45] Feb. 17, 1976

[54] ARRANGEMENT FOR CONTROLLING THE VISCOSITY OF A FLUID

[75] Inventor: Adriaan de Bok, Leerdam, Netherlands

[73] Assignee: ITT Industries, Inc., New York, N.Y.

[22] Filed: Apr. 24, 1974

[21] Appl. No.: 463,703

[30] Foreign Application Priority Data
May 4, 1973  Netherlands.................... 7306289

[52] U.S. Cl..................................... 73/55; 137/87
[51] Int. Cl.² ................................... G01N 11/04
[58] Field of Search ................................. 73/55

[56] References Cited
UNITED STATES PATENTS

| | | | |
|---|---|---|---|
| 1,534,091 | 4/1925 | Smoot.................... | 73/55 X |
| 1,654,614 | 1/1928 | Smith..................... | 73/55 X |
| 2,771,770 | 11/1956 | Bouman................. | 73/55 |
| 3,024,643 | 3/1962 | Jones, Jr................ | 73/55 |
| 3,115,768 | 12/1963 | Rhodes et al. ........ | 73/55 |
| 3,116,630 | 1/1964 | Piros..................... | 73/55 |
| 3,234,781 | 2/1966 | Bragg.................... | 73/55 |
| 3,610,026 | 10/1971 | Topham................. | 73/55 |

FOREIGN PATENTS OR APPLICATIONS

| | | | |
|---|---|---|---|
| 746,340 | 3/1956 | United Kingdom..... | 73/55 |
| 26,837 | 3/1970 | Japan..................... | 73/55 |
| 189,603 | 1/1967 | U.S.S.R................. | 73/55 |

*Primary Examiner*—Jerry W. Myracle
*Assistant Examiner*—Joseph W. Roskos
*Attorney, Agent, or Firm*—John T. O'Halloran; Menotti J. Lombardi, Jr.; Peter van der Sluys

[57] ABSTRACT

A constant output pump delivers a portion of a fluid, the viscosity of which is to be controlled, into a measuring capillary tube to develop a pressure differential across the measuring capillary tube. Means are provided to sense the pressure differential and control the fluid viscosity in response thereto. A second capillary tube is adapted to receive all of the fluid discharged from the measuring capillary tube and an elastic fluid space is interposed between the measuring capillary tube and the second capillary tube. The flow resistance of the second capillary tube and the elasticity of the fluid space functions to make the pressure differential independent of static fluid pressure changes.

9 Claims, 5 Drawing Figures

ARRANGEMENT FOR CONTROLLING THE VISCOSITY OF A FLUID

BACKGROUND OF THE INVENTION

1. Field of the Invention

The invention relates to an arrangement for controlling the viscosity of a fluid having a constant output pump and a measuring capillary tube through which said output is forced, in which the differential pressure of said fluid between the beginning and the end of said capillary tube is used as a control signal so as to influence the viscosity of that fluid.

2. Description of the Prior Art

The prior art is shown in U.S. Pat. No. 2,771,770, which patent discloses a capillary tube viscosity meter, the output signal of which is used so as to automatically control viscosity. Said viscosity meter can readily be installed in a pipe line so that the viscosity of the fluid flowing in this line will be measured under the temperature actually present in the line, there being no need for extracting fluids out of said line for measuring purposes. In said known capillary tube viscosity meter a fluid, the viscosity of which has to be measured, is forced through a measuring capillary tube, the pressure difference of the fluid at the beginning and the end of the measuring capillary tube being measured. The pump and the capillary tube are integrated in such a way, that they can be arranged within the line, consequently they are surrounded by fluid flowing in the line, while the suction inlet of the pump and the outlet end of the capillary tube are in direct communication with the interior of the line.

Such viscosity meter can be easily installed in a line which supplies the heated fuel to a fuel burner installation or an injection internal combustion engine; in such systems not only proper operation but also the power consumption of the high pressure pump depend strongly on the viscosity of the fuel, so the fuel is heated in order to reach the wanted low viscosity. The known viscosity meter is adapted to continually measure the viscosity at the temperature actually present in the fluid line or to control the viscosity because whether in the pump nor in the capillary tube a decrease in temperature of the fluid will occur.

The above, however, has the drawback that the accuracy of the viscosity measurement also depends on the static pressure at the point where the fluid discharges from the measuring capillary tube. Until now the pressure variations in the static pressure were restricted, but recently fuel systems are used having automatic means such as self cleaning filters, which introduce relatively high, partly periodic, pulse-shaped pressure variations in the fuel system. In the prior art viscosity control system these pulsations, which are superimposed on the proper control signal, are transferred onto the means which influence the viscosity of the fluid. Generally, in such control systems the first means is a differential pressure transmitter. This differential pressure transmitter is influenced by the pulsations in a non-linear way. As a result, errors are introduced in the processing of said control signal and under serious conditions the differential pressure transmitter could be forced completely out of its normal linear control range.

SUMMARY OF THE INVENTION

It is an object of the present invention to provide a viscosity control system which is not effected by slow or pulse-shaped variations in the static pressure of the fluid at the point where the fuel used for the measuring rejoins the main flow.

For attaining this object the invention provides for a second capillary tube through which the fluid discharged from the measuring capillary tube is forced and that a fluid space is interposed between the measuring capillary tube and said second capillary tube and that the fluid space has elastic properties.

It is a further object of the present invention to provide for low cost capillary tubes which can be readily connected and can be arranged in a small space.

To this end the arrangement according to the present invention is characterized in that both capillary tubes have the configuration of grooves in the outer surface of a first member, said grooves being covered by a second member.

It is still another object of the present invention to provide means for readily matching the magnitude of the differential pressure which corresponds to a predetermined viscosity to the means which act upon the viscosity of the fluid.

According to a further characteristic of the present invention, said second member has a recess at his covering side which covers a greater or smaller portion of the measuring capillary tube by shifting the second member relative to the first one.

The above and other objects and characteristics of the invention will be better understood from the following detailed description of an embodiment in conjunction with the accompanying drawings in which:

DESCRIPTION OF THE INVENTION

Figure 1:
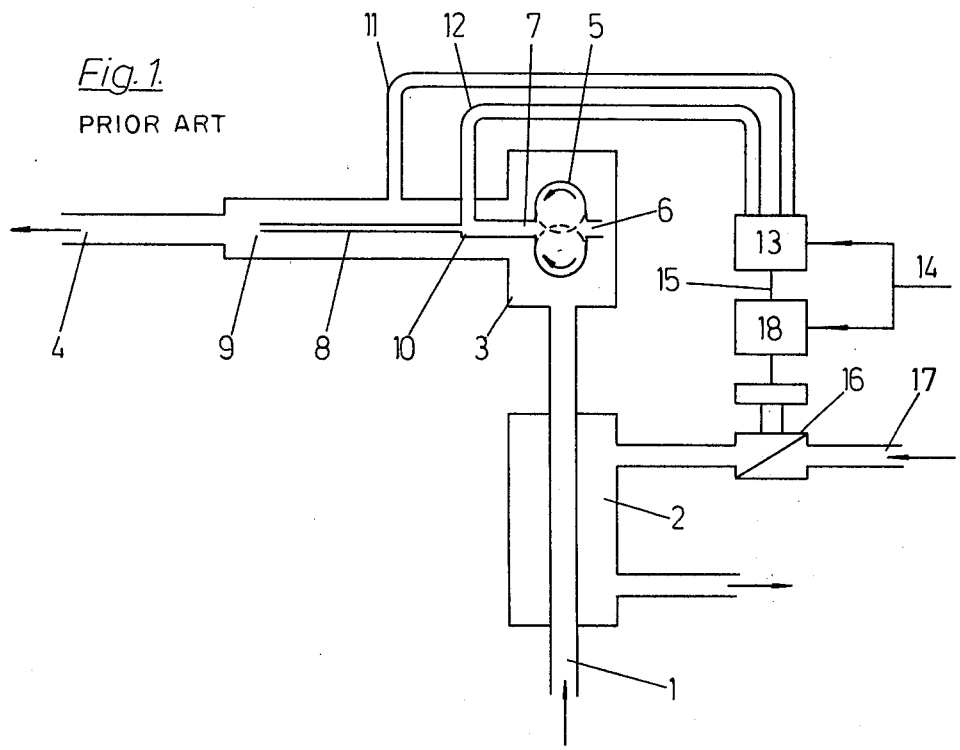
FIG. 1 is a schematic view of a known arrangement for the control of the viscosity.

Referring to FIG. 1, the prior art viscosity control system is used in a fuel supply system for a fuel burner installation or an injection internal combustion engine. Fuel is being supplied at 1 and is heated in a steam-heater 2 to a temperature for a rated viscosity. Fuel then passes to the viscosity measuring unit 3 and subsequently through the fuel line 4 to the high pressure pump, not shown. The viscosity measuring unit 3 principally consists of a small gear pump 5 which sucks at 6 a constant volume of fuel, forces the same through conduit 7 and through the capillary tube 8. Between points 10 and 9 a pressure drop across the capillary tube builds up, being a measure for the viscosity of the fuel. Said pressure difference is transferred through measuring lines 11 and 12 to the differential pressure transmitter 13. Said differential pressure transmitter 13 can be considered as an amplifier and a matching means which converts a relatively small pressure difference between measuring lines 11 and 12 into a control signal adapted to control the pneumatic control station 18. Said pneumatic control station compares the incoming control signal with a standard signal, the present differences being used after amplification so as to adjust the position of the control valve to return the measured value to the set point. To this end, the control valve 16 is arranged in line 17 supplying a heating fluid to fuel heater 2, thus raising fluid temperature and consequently controlling fuel viscosity. Power for operating the differential pressure transmitter 13 and control station 18 is being supplied by pressed air supply 14.

As already mentioned above said prior art system shows the inherent drawback in that periodic pulsations in the fuel supply are transmitted through line 11 to the pressure difference transmitter, affecting the same in a non-linear way. Consequently, the control operation is affected and in worse circumstances control can break down completely.

Figure 2:
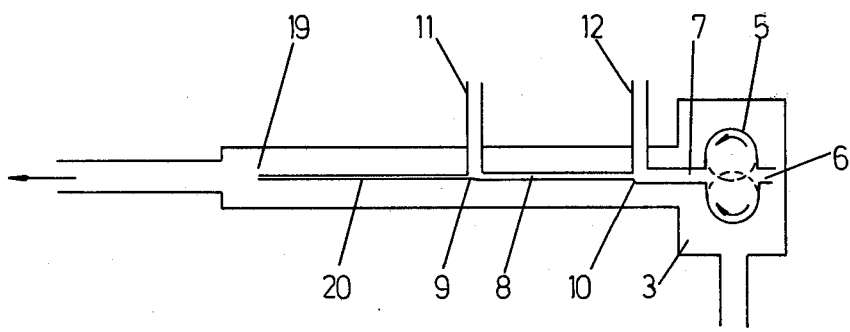
FIG. 2 is the measuring part of the arrangement according to the invention.

In order to provide proper control of viscosity even in fuel systems having high pulsations, according to the invention the prior art viscosity measuring unit 3 shown in FIG. 1 is replaced by the one shown in FIG. 2.

Referring to FIG. 2 in the viscosity measuring unit 3 a small gear pump 5 sucks a constant volume of fluid from the fuel line through suction inlet 6 and is forcing the sample through conduit 7 into the measuring capillary tube 8. Just as in the prior art device the pressure difference building up across the measuring capillary tube 8 between 10 and 9 is a measure for the viscosity of the fuel. According to the present invention, the measuring capillary tube 8 is connected to a damping capillary tube 20 at point 9 so that fluid being passed by the gear pump only discharges at 19 in the main flow. The pressure difference over measuring capillary tube 8 is transmitted through lines 11 and 12 and to the differential pressure transmitter 13. Damping capillary tube 20 operates in cooperation with a fluid space connected to point 9 said fluid space having elastic properties to dampen pulsations present at outlet 19 so that they are not propagated into the measuring lines 11 and 12 and the differential pressure transmitter. The fluid space comprises the measuring line 11 and the differential pressure transmitter 13 while the elastic properties thereof are provided by three contributing factors namely the elasticity of the fuel in the measuring line 11, the inherent resilience of the measuring line itself and the bellows system in the differential pressure transmitter 13. Consequently, viscosity control is no longer affected by slow or fast variations in pressure in the fuel system. In order to raise the damping action, the flow resistance of damping capillary tube 20 should be designed as high as possible.

It should be noted that damping of pulsations in the fuel system with respect to the control could as well be provided by arranging capillary tubes for instance in the measuring lines 11 and 12, however, this introduces high time lags which could affect viscosity control seriously. No such deterioration in time lag exists in the device according to the invention.

Figure 3:
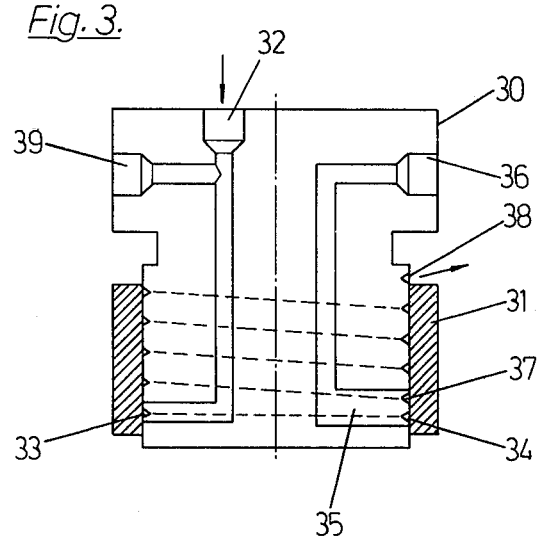
FIG. 3 is a longitudinal sectional view of a capillary system according to the present invention.

Fitting the damping capillary tube of the present invention and especially the jointing the same to the measuring capillary tube, is complicated if conventional capillary tubes having circular cross sections would be used. A capillary system which can be manufactured in a relatively simple way, which is compact, has a great flexibility in the choice in length and cross section of various capillary tubes and to which joints could be readily made, is shown in the embodiment of FIG. 3. This figure shows a longitudinal cross section of the measuring unit comprising a cylindrical member 30 and surrounded by the sealing ring 31. The capillary tubes consist of principally triangular grooves in the outer surface of the cylindrical member, which grooves can be arranged in the outer surface circularly or helically. The fuel supplied by the gear pump is supplied at port 32 and passes through a bore in the cylindrical member 30 into the beginning of the measuring capillary tube 33. The measuring capillary tube 33 extends on a semi-circle to the end 34 of measuring capillary tube, which communicates with bore 35. Said bore 35 communicates at the one side through port 36 with measuring line 11 (FIG. 2) and at the other side with the damping capillary tube 37. Said damping capillary tube 37 extends helically on the cylindrical member 30 and communicates at its end 38, where the ring 31 terminates, with free space. In this case free space is the inner of the fuel line because the present compact embodiment of the capillary tube system together with the gear pump are installed such, that they are substantially surrounded by the fuel. Measuring line 12 (FIG. 2) is sealed in port 39.

It is also possible to enlarge the cylindrical member 30 in an upward direction, the gear pump then being arranged within said member so that port 32 can be dispensed with.

Figure 4:
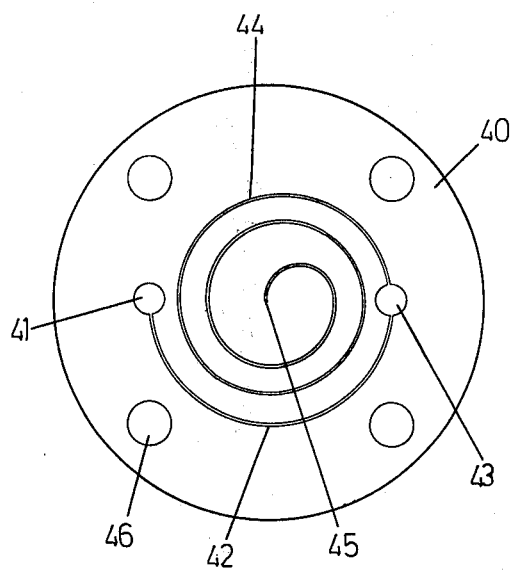
FIG. 4 is a top view of a further embodiment of the first portion of the capillary assembly and FIG. 5 is a top plan view of a sealing plate of the capillary assembly of FIG. 4.
Figure 5:
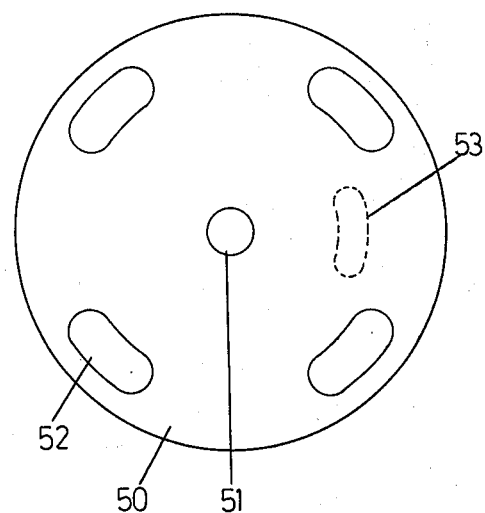

FIGS. 4 and 5 show a further embodiment of the capillary tube system. FIG. 4 is the top plane view of the flat surface of a cylindrical member 40. Similarly to the above embodiment the capillary tubes consist of principally triangular grooves in the end surface of the cylindrical member, said grooves being covered by a sealing plate 50, shown in FIG. 5. The bore 41 of FIG. 4 is connected to the pressure outlet of the gear pump and also to the measuring line 12 (FIG. 2). At the front side bore 41 communicates with groove 42, forming the measuring capillary tube. Said capillary tube 42 extends into a bore 43 which bore communicates at the rear side with measuring line 11 (FIG. 2). The damping capillary tube 44 extends spirally, starting from bore 43, to the center of the end surface. Fuel passes from the end of damping capillary tube 45 through bore 51 in the sealing plate of FIG. 5 into the space. Sealing plate 50 of FIG. 5 is fixed by means of four screws through bores 46 to the body 40 in FIG. 4, bores 52 being aligned with bores 46.

The bores 52 being slot-shaped, it is possible to rotatably shift the sealing plate 50. Accordingly recess 53, arranged in the rear surface of the sealing plate will overlap a smaller or greater portion of the measuring capillary tube 42. In this way, it is possible to increase or decrease the effective length of the measuring capillary tube 42. Consequently, a predetermined viscosity will correspond to a higher or a lower differential pressure. In this way it is possible to match this differential pressure to a value required by the differential pressure transmitter or any other means connected to the capillary tube system. Said means could be a differential pressure indicator having a viscosity dial. Calibration of said indicator can be performed by rotationally adjusting the sealing plate 50.

Instead of arranging capillary tubes in the flat surface of the cylindrical member 40, a thin plate can be sandwiched between member 40 and sealing plate 50, having a thin continuous opening, the configuration of which is similar to the grooves shown in FIG. 4.

While the principals of the invention have been described above in connection with specific apparatus, it is to be understood that this description is made only by a way of example and not as a limitation on the scope of the invention.

What is claimed is:

1. A system for controlling the viscosity of a fluid, comprising:
   a constant output pump for pumping at least a portion of the fluid;
   a measuring capillary tube through which the output of the pump is forced to develop a differential pressure along said measuring capillary tube;
   means for sensing the differential pressure in said capillary tube and for developing a control signal for controlling the viscosity of said fluid;
   a second capillary tube associated with the measuring capillary tube for receiving the fluid discharged therefrom; and
   means for providing an elastic fluid space connected to a point between the measuring capillary tube and the second capillary tube, whereby said elastic fluid space cooperates with the resistance of the second capillary tube to dampen variations in the static pressure of the fluid so that the differential pressure in the measuring capillary tube is not effected thereby.

2. A system as described in claim 1, wherein the flow resistance of the second capillary tube is considerably greater than that of the measuring capillary tube.

3. A system according to claim 1, wherein the capillary tubes are formed by grooves formed in the outer surface of a first member and a second member covering said grooves to form the tube.

4. A system as described in claim 3, wherein the cross section of a groove is substantially triangular in shape.

5. A system as described in claim 3, wherein fluid connection with the grooves is made by means of ducts formed within at least one of said first and second members.

6. A system as described in claim 3, wherein the first member is cylindrically shaped having the grooves extending about the cylindrical surface.

7. A system as described in claim 6, wherein the grooves extend helically.

8. A system as described in claim 3, wherein the outside surface of said first member is a flat surface having the grooves formed therein.

9. A system as described in claim 3, wherein said second member has a recess in its covering side, said recess being formed and arranged to cover a greater or smaller portion of the measuring capillary tube when the second member is shifted relative to the first member.

* * * * *